(12) United States Patent
Decitre

(10) Patent No.: US 8,232,797 B2
(45) Date of Patent: Jul. 31, 2012

(54) DEVICE WITH SEPARATE EMISSION/RECEPTION FUNCTIONS FOR MAKING EDDY CURRENT TESTS ON AN ELECTRICALLY CONDUCTING PART

(75) Inventor: Jean-Marc Decitre, Marcoussis (FR)

(73) Assignee: Commissariat a l'Energie Atomique, Paris (FR)

( * ) Notice: Subject to any disclaimer, the term of this patent is extended or adjusted under 35 U.S.C. 154(b) by 449 days.

(21) Appl. No.: 12/376,114

(22) PCT Filed: Jul. 30, 2007

(86) PCT No.: PCT/EP2007/057847
§ 371 (c)(1),
(2), (4) Date: Nov. 10, 2009

(87) PCT Pub. No.: WO2008/015195
PCT Pub. Date: Feb. 7, 2008

(65) Prior Publication Data
US 2010/0109658 A1  May 6, 2010

(30) Foreign Application Priority Data

Aug. 3, 2006 (FR) ...................... 06 53275

(51) Int. Cl.
*G01R 33/14* (2006.01)
(52) U.S. Cl. ...................................................... 324/222
(58) Field of Classification Search .................. None
See application file for complete search history.

(56) References Cited

U.S. PATENT DOCUMENTS

| | | |
|---|---|---|
| 5,047,719 A | 9/1991 | Johnson et al. |
| 5,182,513 A | 1/1993 | Young et al. |
| 5,506,503 A * | 4/1996 | Cecco et al. ............... 324/220 |
| 5,659,248 A | 8/1997 | Hedengren et al. |
| 2004/0178790 A1 | 9/2004 | Gifford et al. |

FOREIGN PATENT DOCUMENTS

| | | |
|---|---|---|
| EP | 0228177 A2 | 7/1987 |
| FR | 2424515 | 11/1979 |

* cited by examiner

*Primary Examiner* — Paresh Patel
(74) *Attorney, Agent, or Firm* — Nixon Peabody LLP

(57) ABSTRACT

A device with separate emission/reception functions for making eddy current tests on an electrically conducting part comprising several emission rows (1-4) composed of emission windings (55), and several reception columns (a-h) each composed of reception windings (56) connected in series in at least one series, in which the emission windings associated with the reception windings in one series are powered by currents at different frequencies.

18 Claims, 3 Drawing Sheets

DEVICE WITH SEPARATE EMISSION/RECEPTION FUNCTIONS FOR MAKING EDDY CURRENT TESTS ON AN ELECTRICALLY CONDUCTING PART

CROSS REFERENCE TO RELATED APPLICATIONS OR PRIORITY CLAIM

This application is a national phase of International Application No. PCT/EP2007/057847, entitled "DEVICE FOR CHECKING USING EDDY CURRENTS WITH SEPARATE EMISSION/RECEPTION FUNCTIONS AN ELECTRICALLY CONDUCTING PART", which was filed on Jul. 30, 2007, and which claims priority of French Patent Application No. 06 53275, filed Aug. 3, 2006.

TECHNICAL FIELD

The invention relates to a device with separate emission/reception functions for making eddy current tests on an electrically conducting part.

STATE OF PRIOR ART

The field of the invention is eddy current tests on an electrically conducting part with separate emission/reception functions, with a wide operating range using a very compact set of emission and reception windings. Such a test is particularly advantageous for the detection of small defects, particularly for non-destructive testing (NDT) of electrically conducting parts.

The principle of using eddy currents to detect defects in an electrically conducting part consists of using an emission winding to emit an electromagnetic field at a frequency adapted to the conductivity of the material and the depth of the defects being searched for, close to this part. The next step is to measure an electromotive force at the terminals of at least one reception winding, generated by direct coupling of magnetic field lines between the emission winding and the reception winding in the presence of the conducting part. A small variation in this electromotive force that is superposed on it when a defect is present in the material is also measured. The field of the invention is thus restricted to devices using at least one winding assigned to emission of the electromagnetic signal capable of generating eddy currents in the part to be tested, and at least one winding assigned to reception of signals induced by the eddy currents, such a configuration being said to have "separate functions".

The induced electromotive force $V_R$ at the terminals of each reception winding, that is at the same frequency as the current sent into the associated emission winding, is used to obtain the useful signal after demodulation. In the presence of a defect, this induced electromotive force $V_R$ becomes $V_R \pm \delta V_R$, and only the variation $\delta V_R$ that is very small compared with $V_R$, carries information. In practice, as the voltage $V_R$ reduces in comparison to $\delta V_R$, the signal amplification becomes more effective and the signal-to-noise ratio of the measurement improves.

A large number of elements uniformly spaced on the same support can be arranged, to limit the time for inspection of part surfaces and minimise costs necessary for the purchase of one or several mechanical benches with one or several axes frequently requiring high precision. A module (possibly with elements arranged staggered on several rows if a scanning pitch smaller than the size of the element is required) is obtained that only requires a single mechanical displacement along a single axis. It is even possible to create matrices of elements to obtain a direct image of the zone to the tested and thus eliminate slow and expensive precision mechanical displacements. When there are no defects, it is advantageous to have configurations with voltages as similar as possible at the terminals of the different receiving channels so as to facilitate balancing the eddy current testing device demodulating the channels, in order to make the best use of responses from the different elements.

But the use of a large number of elements creates a connection problem. One solution according to prior art disclosed in document reference [1] at the end of this description uses a method that uses separate emitter/receiver type elements arranged in a matrix, and consists of putting rows of emission windings in series, and columns of reception windings in series. Such an arrangement can reduce the number of connections and turns created by connection wires, while maintaining the possibility of querying all elements. However, if defects with small dimensions are to be detected, elements have to be arranged very close to each other such that the defect will be detected by at least one element during acquisition, regardless of its position in the zone to be inspected. Also, since emission windings on a particular row are in series, emission windings close to a given element will disturb this element. The following are added at the terminals of the reception winding of said element considered:

The induced EMF (electromotive force) originating from the associated emitter: VR (element mutual) and $\delta V_R$ (useful signal)

EMF values induced by all magnetic fields radiated by active adjacent emission windings (in other words through which a current passes at the same frequency). In practice, the electromagnetic field decreases with distance and only one or two adjacent elements will have an influence on the receiving winding considered.

Thus, since reception windings are in series, simultaneous power supply of several rows of emission windings is not sufficient to find specific information detected by each element, and therefore a multiplexer has to be used to connect the current or voltage source to each of the emission windings rows in sequence.

Furthermore, if it is impossible to put elements sufficiently far from each other on a single row, coupling (or interference between elements) will tend to increase the voltage at the terminals of the reception windings, which is prejudicial to interpretation of the useful signal $\delta V_R$. Furthermore, this voltage induced in the absence of any defects by the different adjacent emission windings may be different in two different rows of reception windings.

The purpose of the invention is to correct such disadvantages by proposing a device with separate emission/reception functions for making eddy current tests on an electrically conducting part to evaluate the response of a large number of elements simultaneously and independently of each other.

PRESENTATION OF THE INVENTION

The invention relates to a device with separate emission/reception functions for making eddy current tests on an electrically conducting part, comprising several emission rows composed of emission windings, and several reception columns each composed of reception windings connected in series in at least one series, characterised in that the emission windings associated with the reception windings in one series are all powered by currents at different frequencies.

In a first configuration, the emission windings on a single row carry a current with the same frequency. Advantageously, two emission windings on the same emission row separated by one emission winding, have opposite winding directions. The winding direction of reception windings can all be the same or they may be such that two reception windings separated by one reception winding on each reception column, have opposite winding directions. Advantageously, additional emission windings can be arranged at the two ends of each emission row.

In a second configuration, emission windings with an even rank and emission windings with an odd rank on each emission row are powered by different frequency currents, and the reception windings on each reception column are arranged between two adjacent emission windings in the same emission row. Advantageously, at least one additional column of reception windings is arranged in series at the end of each emission row.

Advantageously, the emission rows and reception columns are arranged on each side of a support in both of these two configurations.

For these two configurations, the device according to the invention may advantageously comprise:
amplifiers each arranged at the input to one of the emission rows,
one or several connector(s), for example requiring zero insertion force,
pre-amplifiers, each arranged at the output from one of the reception columns,
a multiplexing system for the reception part.

We can also have:
emission windings in two consecutive rows with opposite winding directions;
reception windings in two consecutive columns with opposite winding directions;
columns of reception windings wired in differential;
excitation frequencies, each of which is a sum of several frequencies.

DETAILED PRESENTATION OF PARTICULAR EMBODIMENTS

Figure 1A:
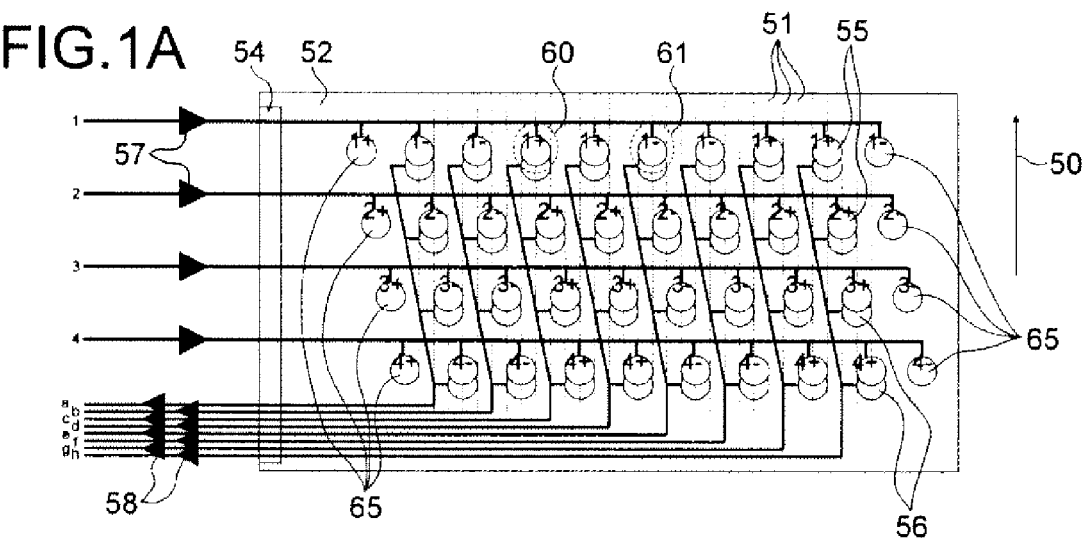
FIGS. 1A to 1E show a top view of a first multi-element configuration of the device according to the invention.
Figure 2A:
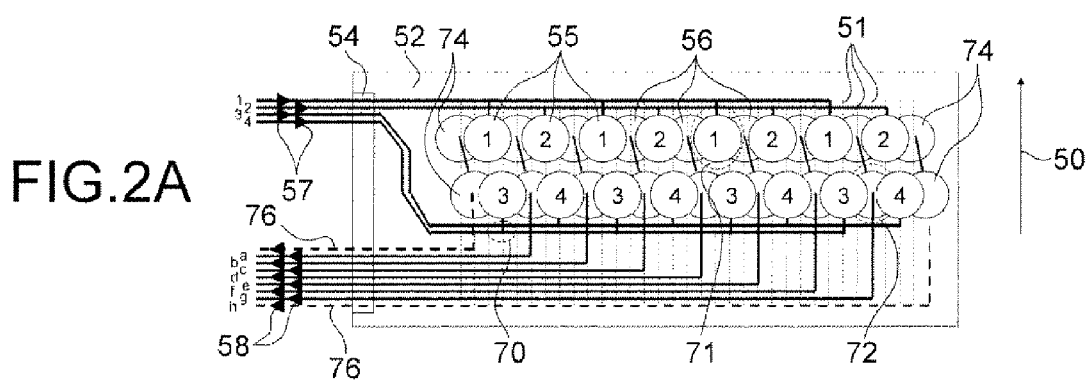
FIGS. 2A to 2D show a top view of a second multi-element configuration of the device according to the invention.

As shown in FIGS. 1A and 2A, the device according to the invention is a device with separate emission/reception functions for making eddy current tests on an electrically conducting part, comprising several emission rows 1-4 composed of emission windings 55, and several columns a-h composed of reception windings 56 connected in series to each other on the same column in at least one series, in which the emission windings associated with the reception windings in the same series on the same column are all powered by currents at different frequencies f1, f2, f3, f4.

Therefore, the device according to the invention is a multi-element configuration used to perform a demodulation step specific to eddy current techniques in parallel, simultaneously for each element and independently of adjacent elements.

As shown in FIGS. 1A and 2A, the device according to the invention comprises a duplicate element in the form of "multi-row module". An "element" means the assembly composed of an emission winding 55 and a reception winding 56.

For a regular matrix configuration that does not require any mechanical displacement, the same arrangement types are possible with elements placed in a square or triangular grid.

The invention can be used firstly to query each row independently using distinct working frequencies. It also limits coupling between the elements in the same row through the use of clearly defined winding directions of the emission and reception windings, and advantageously can even obtain the same coupling value regardless of the column.

First Configuration

A first configuration of the device according to the invention shown in FIG. 1A, comprises four rows of eight distinct elements, represented by an overlap of emission windings 55 and reception windings 56. The arrow 50 shows the direction of displacement of the device according to the invention. All elements are equidistant at a pitch p along the direction perpendicular to the displacement 50. By moving the support 52 along the direction 50, the device acquires measurement points at the spacing of this pitch p. The vertical lines 51 materialise the response of elements during displacement of the device. Advantageously, connection tracks corresponding to the emission windings and reception windings may be arranged on opposite sides of the support 52.

In this first configuration, the emission windings 55 are put in series for each row numbered 1 to 4. The reception windings 56 are put in series for each column numbered a to h. The windings 55 and 56 that can be arranged on opposite side of a support 52, form numbered elements (i, j) where i is the row number varying from 1 to 4 and j is the column number varying from a to h.

The triangles 57 and 58 represent electronic amplifiers, namely four amplifiers 57 on emission lines 1 to 4 and eight reception pre-amplifiers 58, advantageously with low noise, on the reception columns a to h. A single or double face connector 54 may be placed on the support 52 to enable a connection between the connection tracks on the support and the processing electronics (amplifications, multiplexing, demodulation, etc.). The amplifiers and possibly multiplexers or demultiplexers may be placed on one and/or the other of the support faces 52.

In this first configuration, the number of distinct frequencies is chosen to be equal to the number of reception windings in series on a column (four frequencies denoted f1 to f4 in the example). Signals output by the four elements are added at distinct frequencies. Thus, four demodulations (simultaneous or possibly sequential) at these four frequencies f1 to f4 are used on each of the eight reception channels to deduce independent responses of the four elements in the column. Frequencies f1 to f4 are usually chosen fairly close so that responses of the element (VR and δVR) are identical at these frequencies. It is also possible to work at several simultaneous frequencies.

For a given application in which there are small defects opening onto the surface, it would for example be possible to work at a frequency of 10 MHz. For example, in the case of the configuration considered above, we could choose f1=9.8 MHz, f2=9.9 MHz, f3=10.0 MHz and f4=10.1 MHz.

Figure 1B:
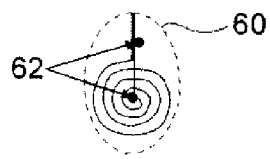
Figure 1C:
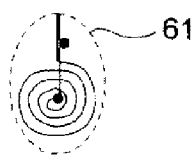

In this first configuration, interference between windings on the same row is also corrected by choosing clearly defined winding directions. The effects of emission windings in the two elements located immediately to the right and the left of a reception winding and on the same row (for example emission windings of elements (2, b) and (2, d) on each side of the reception winding of element (2, c)) will be cancelled out by choosing opposite winding directions for these two emission windings. The magnetic fields created by the emission windings immediately adjacent to this reception winding have the same amplitude but with opposite directions, and consequently cancel out at the reception winding (for example all reception windings may be wound in the same direction). FIGS. 1B (+ direction) and 1C (− direction) show the winding directions of the emission windings located at 60 and 61, and points 62 show metallised holes. Thus, all elements on each row are located between two elements, one being one turn of the emission winding in the + direction and the other one turn of the emission winding in the − direction. Additional emission windings 65 can be added at the two ends of each row 1, 2, 3 and 4 wound in the opposite direction of the adjacent emission winding located on the same row, so as to prevent any edge effects and to obtain the same voltage regardless of the reception winding column considered (which facilitates the balancing phase of the eddy currents instrument).

In one advantageous embodiment, an element composed of an emission winding 55 and a reception winding 56 etched on a 50 μm thick kapton film are considered, the two windings each having an outside diameter of 1 mm and an inside diameter of 500 μm and 6 turns. The emission winding is powered by a current of 20 mA with four frequencies very close to 10 MHz. The distance d between the two windings in a particular element is chosen to be equal to 730 μm so as to minimise the mutual and maximise the response due to a typical size of defect to be detected, in this example fixed at a length of 400 μm, a width of 200 μm and a depth of 200 μm. The chosen value of d obtained by simulation or experimentally, leads to an overlap of the windings.

Figure 3:
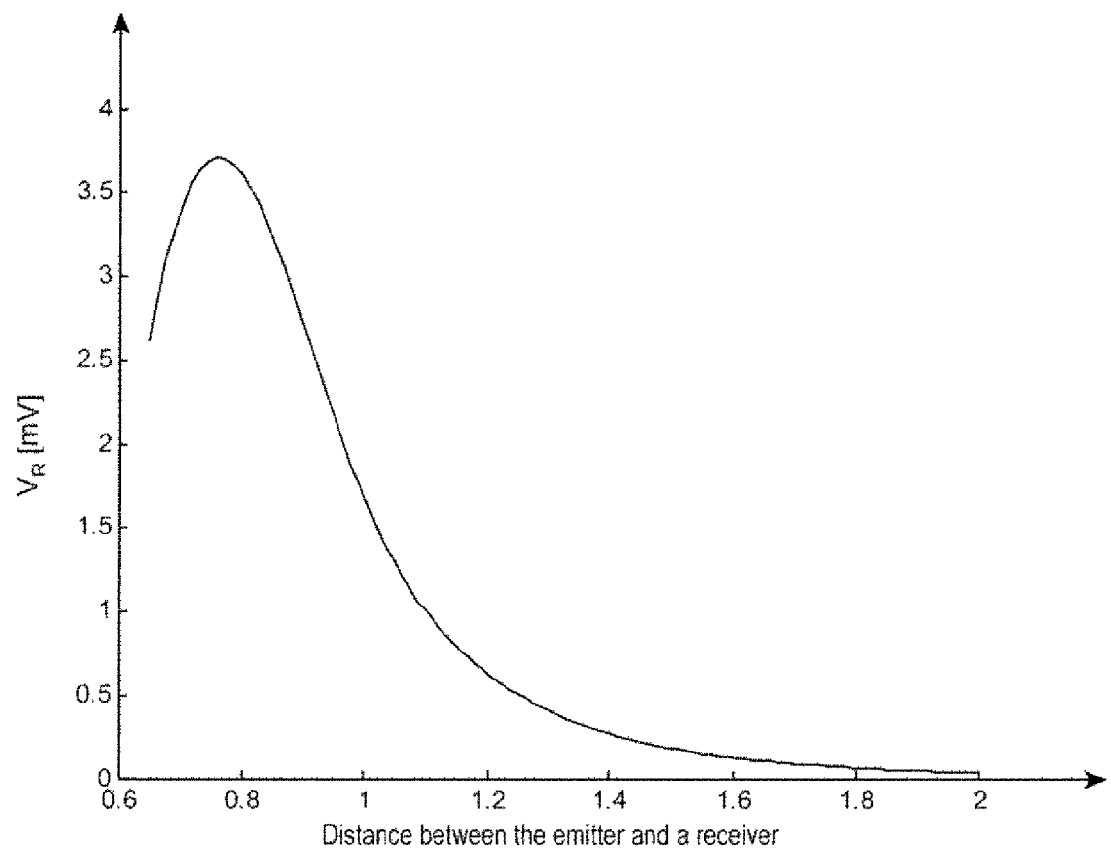
FIG. 3 shows how the modulus of the voltage obtained at the terminals of a reception winding varies as a function of the distance between the reception and an emission winding.

FIG. 3 shows the variation of the mutual VR obtained at the terminals of a reception winding as a function of the distance separating an emission winding and a reception winding in two distinct elements. For the optimised distance of d=730 μm, the mutual VR within an element is equal to 3.26 mV. If it is required to obtain a mutual between two elements equal to 20 dB less than 3.26 mV (namely 326 μV), two adjacent elements (on the same row or the same column) have to be positioned such that the reception winding of one of the elements is at a distance $d_{ER}$=1.65 mm from the emission winding in the other element. It is deduced that the distance between two adjacent elements on the same row must be at least $\sqrt{(d_{ER}^2-d^2)}$=1.48 mm.

For nearby frequencies f1 to f4, we can consider emission windings and/or reception windings in two consecutive rows with opposite winding directions. This means that VR couplings between each of the elements can be at least partially cancelled out, rather than being additive.

First Variant Embodiment

The number of rows of elements in the above example is fixed at 4, so that the rows must be at a spacing of $\sqrt{(d_{ER}^2-d^2)}$=1.61 mm, the pitch p being equal to 350 μm so as to limit coupling between elements in the same column. The size of the device along the displacement axis 50 is equal to $(2 \times r_{ext}+4 \times d+3 \times 1.6)$=8.75 mm ($r_{ext}$: outside radius of windings).

Figure 1D:
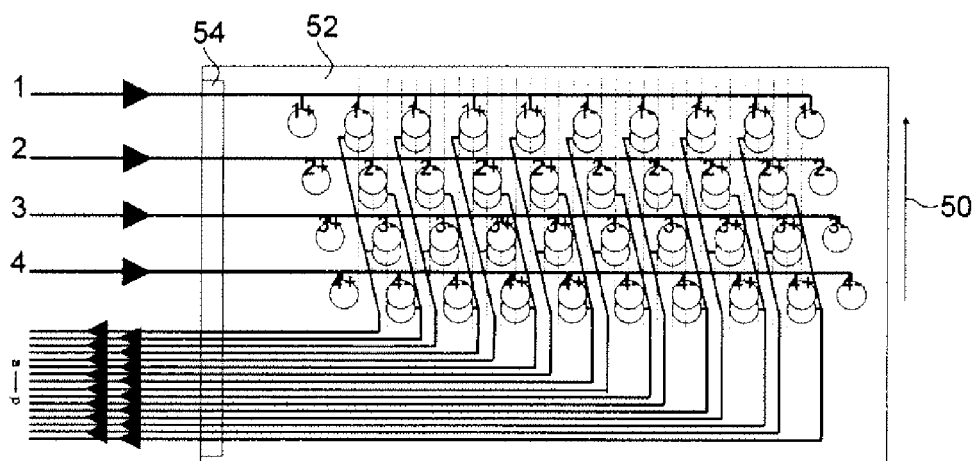

A first variant shown in FIG. 1D consists of connecting one reception winding out of two in series in each of the columns and using twice the number of reception channels, so as to overcome this coupling problem and make smaller sensors in a closely spaced matrix. With the above-mentioned numeric values, the distance for this new arrangement gives a dimension of 6.9 mm instead of 8.75 mm. This variant can be used with only two frequencies, to limit the number of emission frequencies.

Second Variant Embodiment

Figure 1E:
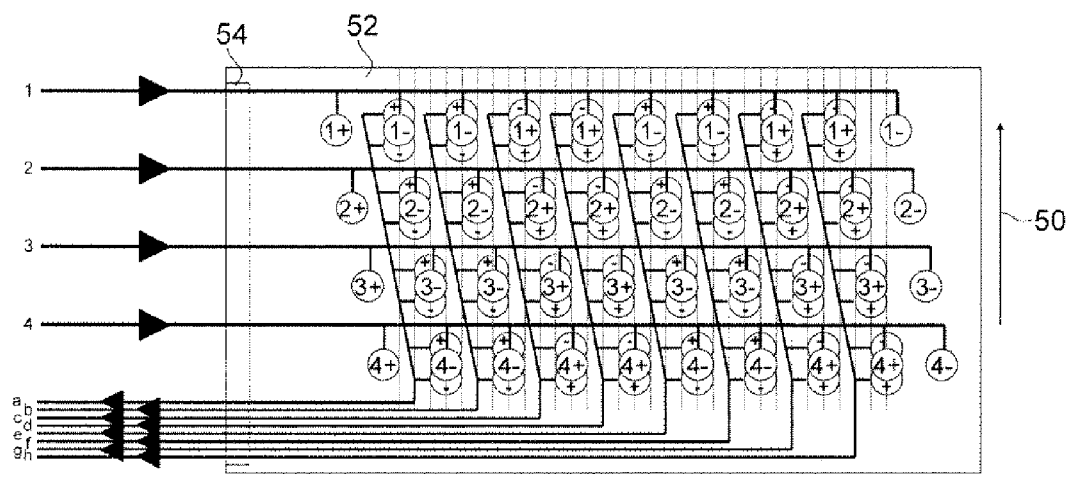

Each element can have various geometries (identical or non-identical emission windings and reception windings, arrangement with or without overlap, coaxial or not), and the emission or reception winding may possibly be broken down into two separate windings connected in series or differentially. FIG. 1E uses the same configuration shown in FIG. 1A, each reception winding now being composed of two windings cabled differentially.

Second Configuration

In a second configuration shown in 2A, the axis of an element defined by the centre of emission and reception windings is oriented at 90° from the displacement 50 of the sensor. The emission windings are arranged on several rows, for example two. The reception windings are arranged on the emission rows and are inserted between two emission windings. The reception windings form columns, and as in the previous configuration they are put in series by column in at least one series.

Thus, a reception winding is associated with the two adjacent emission windings (the winding at the right and the winding at the left) on the same row. Four emission windings are thus associated with each of the columns of the two reception windings. Four distinct frequencies for each of the emission windings are used to separate the signal obtained. Even emission windings and odd emission windings in the same row are powered with currents at distinct frequencies f1 and f2. The columns for which the reception windings are in series are powered by currents with frequencies f3 and f4 different from the frequencies on the previous lines.

An additional reception winding column 74 and its connections (link 76) may be added at either one or both ends of the rows.

All reception windings may be placed on the same face of the support 52 and all emission windings may be placed on the other face of the same support.

Figure 2B:
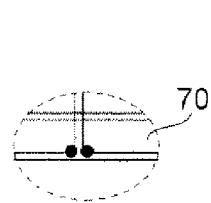
Figure 2C:
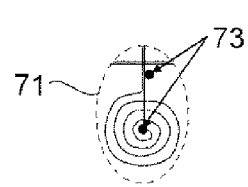
Figure 2D:
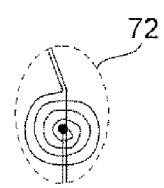

FIG. 2B shows how an emission winding is put into series at 70. FIGS. 2C and 2D show the direction of the corresponding turns of an emission winding 71 with metallised holes 73 and a reception winding 72.

Emission and/or reception windings may have a single turn. In this case, the metallised holes 62, 73 are not necessary. Furthermore, each of the emission windings and the reception windings of an element may be composed of several windings connected in series. For example, a winding may be composed of two coaxial windings etched facing each other on each of the faces of a kapton film and connected in series through the metallised hole, the winding direction being such that the voltages at their terminals are additive. For example, an emission or reception winding may also be composed of two (or more) non-coaxial windings connected differentially at a similar distance from the corresponding emitter.

In this second configuration, with the values in the example considered above, an emission winding of one element is separated from the reception winding of the next element working at the same frequency by 2.1 mm, such that interference on the same row is much better than 20 dB.

This second configuration also has the advantage that it minimises the number of windings on the support. The principle may be extended to a larger number of rows. Differential configurations can also be obtained by differentially wiring two consecutive reception columns.

If frequencies f1 to f4 are close to each other in the device according to the invention, emission windings or reception windings of two consecutive rows may be used with opposite winding directions. This means that couplings of each of the elements can be at least partially cancelled out rather than being additive.

Rows of emission windings may be arranged in series so that each carries an identical current, which minimises response differences between the elements. But in some cases, particularly if the impedance of the emission windings is high and produces a large voltage drop at the terminals of these windings, the electrical source (voltage and current) may not supply the complete row of emission windings correctly. In this case, all emission windings may be arranged in parallel on the same row. Intermediate solutions are possible by wiring a small defined constant number of consecutive emission windings in series and then wiring the assemblies thus formed in parallel.

Several matrices can also be superposed on each other so as to reduce the pitch p between elements, choosing frequencies that do not generate any coupling between the elements in each of the matrices.

Several matrices of elements with configurations identical to those described above can be used to cover large areas, and to be able to supply a large number of emission windings in series. These matrices may be independent from each other. They can also be wired such that the series of emission windings are cabled in series or in parallel and reception windings are cabled in series.

In practice, in eddy current tests, work is often done at several frequencies with a single element sensor. These frequencies are superposed by summating at least two currents or voltages at different frequencies. Therefore, this multi-frequency technique can be used in the configurations presented above. Rows 1 to 4 of emission windings are then not each powered by single-frequency currents f1 to f4, but by a sum of n currents at different frequencies f11 to f1$n$ for row 1, f21 to f2$n$ for row 2, etc. Demodulation is done at each frequency f11, ... f1$n$, f21, ... f2$n$ .... For example, it may be advantageous to work firstly at 10 MHz and secondly at 1 MHz, to be able to evaluate the depth of a defect opening up on the surface. We could then choose f11=9.8 MHz, f12=0.98 MHz, f21=9.9 MHz, f22=0.99 MHz, f31=10 MHz, f32=1 MHz, f41=10.1 MHz, f42=1.1 MHz, these same frequencies being chosen as demodulation frequencies.

The invention claimed is:

1. A device with separate emission/reception functions for making eddy current tests on an electrically conducting part, the device comprising:
   a plurality of emission rows i each composed of emission windings;
   a plurality of reception columns each composed of reception windings connected in series in at least one series; and
   a power supply means for powering the emission windings of the plurality of emission rows i with currents at frequencies fi that are different for each row i,
   wherein said emission windings are associated with reception windings such that the signals received in the reception windings of one column are additively coupled at these different frequencies.

2. Device according to claim 1, in which there is an overlap of emission windings and reception windings.

3. Device according to claim 1, in which the emission windings on a single row carry a current with the same frequency.

4. Device according to claim 3, in which two emission windings separated by one emission winding on each emission row, have opposite winding directions.

5. Device according to claim 3, in which two reception windings separated by one reception winding on each reception column, have opposite winding directions.

6. Device according to claim 3, in which all reception windings on each reception column have the same winding direction.

7. Device according to claim 3, that comprises additional emission windings at the two ends of each emission row.

8. Device according to claim 1, in which emission windings with an even rank and emission windings with an odd rank on each emission row, are powered by different frequency currents, and in which the reception windings on each reception column are arranged between two adjacent emission windings in the same emission row.

9. Device according to claim 8, that comprises at least one additional column of reception windings arranged in series at the end of the emission row.

10. Device according to claim 1, in which the emission rows and reception rows are arranged on each side of a support.

11. Device according to claim 1, that comprises amplifiers each arranged at the input to one of the emission rows.

12. Device according to claim 1, that comprises pre-amplifiers each arranged at the output from one of the reception columns.

13. Device according to claim 1, that comprises one or several connector(s).

14. Device according to claim 13, in which the connector(s) require zero insertion force.

15. Device according to claim 1, in which emission windings in two consecutive rows have opposite winding directions.

16. Device according to claim 1, in which reception windings in two consecutive columns have opposite winding directions.

17. Device according to claim 1, in which columns of reception windings are wired in differential.

18. Device according to claim 1, in which excitation frequencies are a sum of several frequencies.

* * * * *